United States Patent [19]
Penkler et al.

[11] Patent Number: 5,854,226
[45] Date of Patent: Dec. 29, 1998

[54] PHARMACEUTICAL COMPOSITION

[75] Inventors: Lawrence J Penkler; Lueta A Glintenkamp; Douglas G M Nicholson, all of Port Elizabeth; Michiel C B Van Oudtshoorn, Pretoria, all of South Africa

[73] Assignee: Farmarc Nederland BV, Amsterdam, Netherlands

[21] Appl. No.: 849,059

[22] PCT Filed: Nov. 14, 1995

[86] PCT No.: PCT/GB95/02679

§ 371 Date: May 15, 1997

§ 102(e) Date: May 15, 1997

[87] PCT Pub. No.: WO96/14839

PCT Pub. Date: May 23, 1996

[30] Foreign Application Priority Data

Nov. 15, 1994 [ZA] South Africa .......................... 94/9055

[51] Int. Cl.⁶ ..................... A61K 31/715; A61K 31/19
[52] U.S. Cl. .............................. 514/58; 514/570
[58] Field of Search ...................... 514/58, 570

[56] References Cited

U.S. PATENT DOCUMENTS

| | | | |
|---|---|---|---|
| 4,228,160 | 10/1980 | Szejtli et al. ............................. | 424/180 |
| 4,565,807 | 1/1986 | Uekama et al. ......................... | 514/58 |
| 4,603,123 | 7/1986 | Chiesi et al. ............................ | 514/58 |
| 5,019,563 | 5/1991 | Hunter et al. ........................... | 514/58 |
| 5,164,380 | 11/1992 | Carli et al. .............................. | 514/58 |
| 5,206,025 | 4/1993 | Courteille et al. ..................... | 424/439 |
| 5,362,758 | 11/1994 | Ahmed . | |
| 5,376,645 | 12/1994 | Stella et al. ............................. | 514/58 |
| 5,472,954 | 12/1995 | Loftsson ................................. | 514/58 |
| 5,486,508 | 1/1996 | Uda et al. ............................... | 514/58 |
| 5,646,131 | 7/1997 | Badwan et al. ......................... | 514/58 |

FOREIGN PATENT DOCUMENTS

| | | |
|---|---|---|
| 9415930 | 8/1994 | South Africa . |
| 95 04528 | 2/1995 | WIPO . |
| 95 32737 | 12/1995 | WIPO . |

OTHER PUBLICATIONS

Orienti et al., "Availability of NSAIDH β–Cyclodextrin Inclusion Complexes," Arch.Pharm.(Weinheim) 322,207–211 (1989).

Marais et al., "Relationship Between the pH of the Diffusion Layer and the Dissolution Rate of Rurosemide," Drug Development and Industrial Pharmacy, 17(12), 1715–1720 (1991).

CAPLUS abstract, Acc. No. 1992:46126, Saleh et al. Minutes Int. Symp. Cyclodextrins, 5th, 373–380, 1990.

CAPLUS abstract Acc. No. 1991:457201, Hirayama et al., JP 03005438, 1991.

CAPLUS abstract Acc. No. 1989:101599, Erden et al., Int. J. Pharm. 48(1–3), 83–9, 1988.

*Primary Examiner*—Raymond Henley, III
*Attorney, Agent, or Firm*—Pillsbury Madison & Sutro LLP

[57] ABSTRACT

A pharmaceutical composition for oral administration for the treatment of acute pain and inflammation comprises an inclusion complex of a non-steroidal anti-inflammatory drug or a pharmaceutically acceptable salt thereof and a cyclodextrin, and a physiologically acceptable alkali agent selected from the group consisting of alkali and alkaline earth metal carbonates, bicarbonates, phosphates and hydroxides, and water soluble amines, in an amount equivalent to between 2 and 30 molar equivalents inclusive of the non-steroidal anti-inflammatory drug, the alkali agent being capable of forming an alkaline diffusion layer around the composition in the grastrointestinal tract.

12 Claims, 2 Drawing Sheets

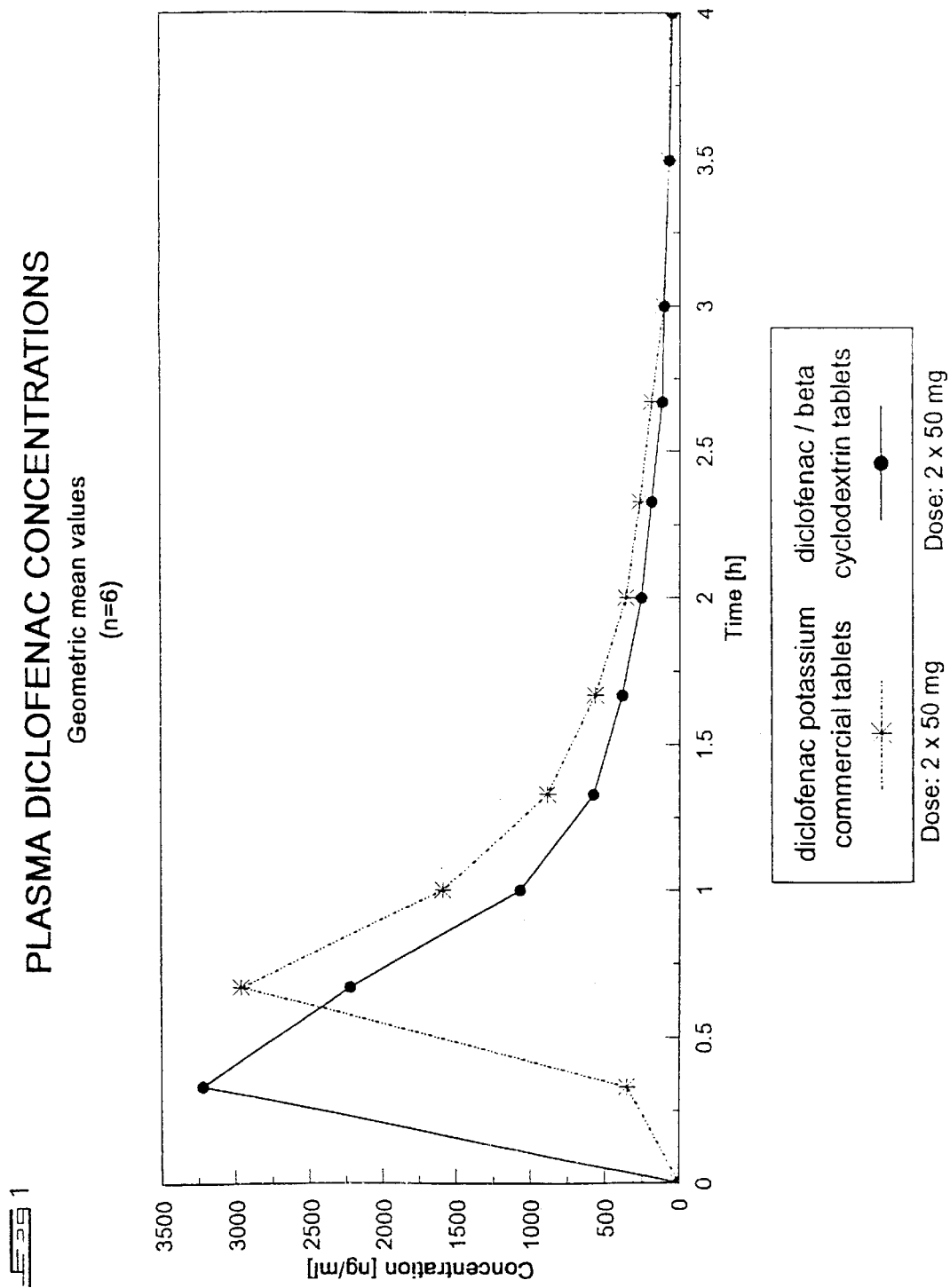

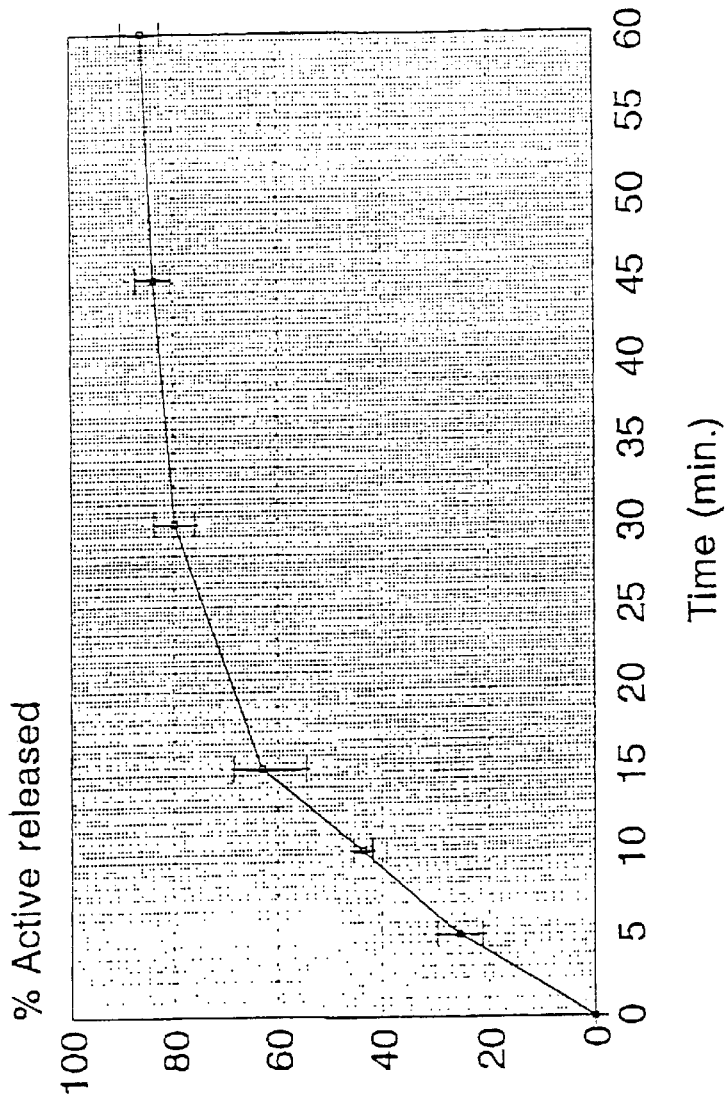

PHARMACEUTICAL COMPOSITION

This application is the national phase of international application PCT/GB95/02679, filed Nov. 14,1997 which was designated the U.S.

BACKGROUND OF THE INVENTION

This invention relates to a pharmaceutical composition for oral administration comprising an inclusion complex of a non-steroidal anti-inflammatory drug (NSAID) and a cyclodextrin, and an alkali agent.

Oral treatment with non-steroidal anti-inflammatory drugs has the disadvantage of gastrointestinal side effects, particularly local gastric irritation. Contact between the NSAID and the mucosa is believed to constitute an important factor in the pathogenesis of gastric irritation [Bianchi, P. G et al. Why are non-steroidal anti-inflammatory drugs important in peptic ulceration? Alimentary Pharmacology and Therapeutics 1987, 1, 5405–5475]. Commercial preparations of NSAID's for oral administration include enteric coated tablets which release the drug in the duodenum so as to avoid local gastric irritation. This however has the disadvantage that peak plasma levels of the drug are reached between one to four hours after administration of the enteric coated tablets.

An example of an NSAID is diclofenac which is a phenylacetic acid NSAID with potent anti-inflammatory and analgesic actions highly utilized in the treatment of acute and chronic pain especially when associated with inflammation e.g. post operative pain, rheumatism, arthritis, gout, musculo-skeletal injury and trauma. In order to reduce the lag-time associated with enteric coated diclofenac tablets, a non-enteric coated tablet and dispersible dosage form have recently been commercialized with indications for short-term treatment of acute inflammatory conditions, although gastro-intestinal side effects are frequent, particularly local gastric irritation [Martindale Extra Pharmacopoeia Edition 30].

There is therefore a need for oral pharmaceutical compositions of NSAIDs e.g. diclofenac, which provide rapid absorption with minimized gastrointestinal irritation.

The properties of cyclodextrins and numerous inclusion complexes are well known and have been reviewed in detail [Szejtli, J. Cyclodextrin Technology (1988) Kluwer Academic Publishers, Dordrecht].

Depending on solvent conditions, a dissolved inclusion complex exists in equilibrium between uncomplexed host and guest and complexed host/guest. Orally administered cyclodextrin-drug inclusion complexes generally result in rapid absorption of the drug, facilitated by the cyclodextrin, whereas the cyclodextrin is not absorbed to any significant extent. Additionally cyclodextrin inclusion complexes of certain drugs have been shown to reduce gastrointestinal side effects [Frömming, K-H & Szejtli, J. Cyclodextrins in Pharmacy (1994), Kluwer Academic Publishers]. Cyclodextrins therefore possess ideal properties as drug carriers. Cyclodextrins and their inclusion complexes possess favourable flow, binding and compaction properties facilitating tablet compression.

The diffusability of a diclofenac (acid) complex with beta cyclodextrin has been reported [Availability of NSAIDH β-Cyclodextrin Inclusion Complexes, Orienti, I., Cavallari, C. and Zecchi, V. Arch. Pharm (Weinheim) 1989, 322, 207–211]. The complex was found to be poorly soluble at pH 2.

The effect of addition of buffering agents to tablet and capsule formulations of sparingly soluble acidic drugs e.g. furosemide, is known to enhance the dissolution rate of the drug in gastric media [Marais, A. F. & van der Watt J. G. Relationship between the pH of the diffusion layer and the dissolution rate of furosemide; Drug Development and Industrial Pharmacy 1991, 17, 1715–1720].

South African Patent No 94/5930 in the name of Smithkline Beecham PLC discloses a pharmaceutical composition for oral consumption in aqueous solution comprising a drug/beta-cyclodextrin complex, wherein the composition further comprises a pharmaceutically acceptable acid-base couple, in a quantity sufficient to cause the drug/beta-cyclodextrin complex to dissolve when the composition is mixed with cold water and provide a solution with acid or neutral pH. It is essential to this pharmaceutical composition that it contain the combination of an acid and a base couple, which may or may not be effervescent.

SUMMARY OF THE INVENTION

According to the invention there is provided a pharmaceutical composition for oral administration comprising an inclusion complex of a non-steroidal anti-inflammatory drug or a pharmaceutically acceptable salt thereof and a cyclodextrin, and a physiologically acceptable alkali agent selected from the group consisting of alkali and alkaline earth metal carbonates, bicarbonates, phosphates and hydroxides, and water soluble amines, in an amount equivalent to between 2 and 30 molar equivalents inclusive of the non-steroidal anti-inflammatory drug, the alkali agent being capable of forming an alkaline diffusion layer around the composition in the gastrointestinal tract.

The NSAID may be any suitable NSAID such as for example diclofenac, indomethacin, naproxen, ibuprofen, mefenamic acid, piroxicam, tenoxicam, lornoxicam, or a pharmaceutically acceptable salt thereof.

The cyclodextrin may be any suitable cyclodextrin but is preferably a beta-cyclodextrin which may be substituted for example with methyl or hydroxypropyl groups, or preferably an unsubstituted beta-cyclodextrin. However, for tenoxicam and lornoxicam, the cyclodextrin is preferably alpha-cyclodextrin.

The alkali agent, when it is an amine, may be selected from ammonium hydroxide, tris(hydroxymethyl) aminomethane, ethanolamine and diethanolamine.

The alkali agent is preferably sodium hydrogen carbonate, also known as sodium bicarbonate, or tris(hydroxymethyl) aminomethane, also known as trometharnine.

The pharmaceutical composition is preferably formulated as a tablet or a capsule.

The pharmaceutical composition may also contain conventional excipients including binders such as starch and microcrystalline cellulose, diluents such as lactose, disintegrating agents such as sodium carboxymethylcellulose, and lubricants.

The NAISD:cyclodextrin inclusion complex preferably has a mass ratio of NSAID:cyclodextrin of between 1:0,85 and 1:5 inclusive, more preferably between 1:1 and 1:2,5 inclusive.

The active component is preferably an inclusion complex of diclofenac optionally in the form of a pharmaceutically acceptable salt such as diclofenac sodium or diclofenac potassium, and an unsubstituted beta-cyclodextrin. The mass ratio of diclofenac to beta-cyclodextrin is preferably between 1:1,8 and 1:9 inclusive, more preferably between 1:3 and 1:5 inclusive. The unit dose of the complex may be equivalent to between 10 and 100 mg inclusive diclofenac, but preferably between 20 and 60 mg inclusive diclofenac.

The active component may also be an inclusion complex of lornoxicam and alpha-cyclodextrin. The mass ratio of lornoxicam to alpha-cyclodextrin is preferably between 1:2,6 and 1:13 inclusive. The unit dose of the complex may be equivalent to between 2 and 10 mg inclusive lornoxicam, but preferably between 4 and 8 mg lornoxicam.

The pharmaceutical composition may also contain at least one further active ingredient such as for example morphine, codeine, propoxyphene or paracetamol, or meprobamate.

The pharmaceutical composition of the invention may be used in the treatment of acute pain and inflammation.

BRIEF DESCRIPTION OF THE DRAWINGS

FIG. 1 is a graph of plasma concentration versus time from Example 3; and

FIG. 2 is a graph of the mean dissolution rate of the tablets of Example 5.

DESCRIPTION OF EMBODIMENTS

The invention relates to a pharmaceutical composition for oral administration comprising an inclusion complex of an NSAID or a pharmaceutically acceptable salt thereof and a cyclodextrin, and a physiologically acceptable alkali agent selected from the group consisting of alkali and alkaline earth metal carbonates, bicarbonates, phosphates and hydroxides, and water soluble amines, in an amount equivalent to between 2 and 30 molar equivalents inclusive of the NSAID, the alkali agent being capable of forming an alkaline diffusion layer around the composition in the gastrointestinal tract.

It is to be noted that the pharmaceutical composition of the invention must not contain any additional acid agent which can form an acid-base couple with the alkali agent, or the alkali agent will not be capable of forming an alkaline diffusion layer around the composition in the gastrointestinal tract.

The incorporation of an alkali agent in the formulation of an NSAID-cyclodextrin complex improves release of the NSAID from the complex in gastric media.

The alkali further functions to neutralize the microenvironment surrounding the disintegrating tablet in the gastrointestinal tract, particularly the stomach, creating an alkaline diffusion layer. When administered to healthy human volunteers, non-enteric coated diclofenac sodium-beta cyclodextrin tablets according to the invention containing diclofenac shows a superior extent of absorption as measured by the area under the data curve (AUDC) parameter when compared with commercial non-enteric coated diclofenac tablets used as reference product. The variable $C_{max}$ extends over the upper bound of the bioequivalence range relative to the reference product and the $T_{max}$ variable is shorter by about 50%. Tablets according to the invention containing diclofenac therefore appear to exhibit an increased rate of absorption relative to the reference product. An increased rate of absorption is likely to reduce contact time between diclofenac and the intestinal mucosa thereby reducing the potential for gastric irritation. In addition, presentation of the drug to the gastric mucosa as an inclusion complex may further reduce gastric irritation. The same effect is applicable to other NSAID's.

An inclusion complex for use in the pharmaceutical composition of the invention may be prepared as follows:

(1) pre-mixture of the required ratios of pre-screened NSAID and cyclodextrin;

(2) transfer to a suitable mixing vessel;

(3) gradual addition of deionised purified water with vigorous mixing until a paste-like consistency is reached;

(4) kneading of the paste for a suitable period of time, for example from 0,25 to 1 hour, with further occasional addition of deionised purified water if necessary to maintain the paste-like consistency until the inclusion complex is formed;

(5) drying the product of step (4); and (6) screening the product of step (5).

To form the pharmaceutical composition of the invention, the inclusion complex is blended with the alkali agent and with suitable excipients and then formed into a suitable oral dosage form such as tablets or capsules.

The preferred active components of the pharmaceutical composition of the invention are an inclusion complex of diclofenac or a pharmaceutically acceptable salt thereof and an unsubstituted beta-cyclodextrin or lornoxicam or a pharmaceutically acceptable salt thereof and alpha-cyclodextrin. Various examples utilising such inclusion complexes will now be given.

EXAMPLE 1

Diclofenac sodium (6,6 g) and beta-cyclodextrin (23,4g) are screened (30 mesh) and tumble mixed. The mixture is transferred to a mortar. Deionised water (10–15 ml) is gradually added with vigourous mixing to produce a uniform paste. Vigorous mixing is continued for 0,5 hours ensuring a uniform paste-like consistency throughout the operation. The mixture is oven dried at 40° C. The dried mass is crushed and passed through 30 mesh screen. The powder is homogenised in a powder mixer for 10 minutes. The product contains 21 % m/m diclofenac sodium as determined by HPLC. The water content of the product is between 9 and 11% m/m as determined by Karl Fisher titration. The molecular composition of the product thus corresponds to 1 molecule diclofenac sodium, I molecule beta cyclodextrin and between 7 and 10 water molecules. The particle size of the product corresponds to 90% less than 30 microns as measured under a light microscope. The morphology of the complex resembles very fine fractured crystalline particles.

EXAMPLE 2

The inclusion complex of beta-cyclodextrin-diclofenac sodium obtained in Example 1 was formulated into tablets with the following unit composition:

| | |
|---|---|
| Diclofenac sodium-beta cyclodextrin complex (equivalent to 50 mg diclofenac sodium) | 220 mg |
| Sodium hydrogen carbonate | 200 mg |
| Microcrystalline cellulose | 130 mg |
| Starch | 44 mg |
| Magnesium stearate | 6 mg |
| | 600 mg |

The sodium hydrogen carbonate, microcrystalline cellulose and starch are premixed in a blender. The diclofenac sodium-beta cyclodextrin complex is added to the mixture and blended. The magnesium stearate is screened in and blended. The mixture is compressed into tablets with a compression force of about 100N. The tablets are optionally film-coated.

EXAMPLE 3

Tablets prepared according to Example 2 were administered to six healthy human volunteers in a double blind cross-over trial against a commercial non-enteric coated diclofenac potassium 50 mg tablet as reference product. Each candidate received 2×50 mg diclofenac products and plasma diclofenac concentration was measured at 20 minute intervals. The pharmacokinetic data is summarized in Table 1 and the plasma concentration versus time curves are shown in FIG. 1 (data from Bioequivalence Study FARMOVS 20/94).

TABLE 1

Summary of Pharmacokinetic data for Diclofenac (n = 6)

| Variable | Unit | Reference Product Dose: 2 × [50 mg diclofenac potassium tablet] Geometric | | | Test Product Dose: 2 × [diclofenac/ betacyclodextrin tablet equivalent to 50 mg diclofenac sodium] Geometric | | |
|---|---|---|---|---|---|---|---|
| | | Mean | SD | Range | Mean | SD | Range |
| $C_{max}$ | (ng/ml) | 3050 | 1,22 | 2253–3825 | 3992 | 1,46 | 2440–6260 |
| $T_{max}$ | (h) | 0,67 | | 0,33–0,67 | 0,33 | | 0,33–0,67 |
| AUDC | (ng.hr/ml) | 2827 | 1,17 | 2423–3631 | 3047 | 1,24 | 2230–3898 |

$C_{max}$ = maximum plasma concentration obtained
$T_{max}$ = time to reach $C_{max}$
AUDC = area under the data curve The test product was well tolerated with no reports of adverse effects. Peak plasma levels of diclofenac from the beta-cyclodextrin complex were obtained within about 20 minutes (mean $T_{max}$=0,33 hr) or half the time required for commercial non-enteric coated diclofenac preparation. The $T_{max}$ for conventional enteric coated diclofenac tablets is significantly longer (one hour or more) owing to lag-time to reach the duodenum. The 90% confidence interval for the mean of the variable $C_{max}$ of the test product extends over the upper bound of the bioequivalence range relative to the reference product and the AUDC value falls within the conventional bioequivalence range of 80 to 125%. The test product is bioequivalent to the reference product with respect to extent of absorption of diclofenac and seems to have a higher rate of absorption than the test product. The formulation according to the invention thus provides diclofenac in a form which is apparently more rapidly absorbed than conventional enteric and non-enteric coated formulations of diclofenac without affecting the extent of absorption. The invention thus has the advantage of providing therapeutic plasma levels of diclofenac in a relatively short time and thus enables a rapid onset of pharmacological action. Apart from the potential gastroprotectant effect created by the cyclodextrin inclusion complex, the apparent increased rate of absorption is likely to decrease the contact time of diclofenac with the gastrointestinal mucosa leading to a reduced extent of local gastric irritation associated with oral diclofenac treatment.

It is proposed that on dilution in the stomach of a tablet according to Example 1, an alkaline diffusion layer created by the alkali is established. The complex rapidly dissolves in the diffusion layer and then diffuses into the bulk fluid where dilution takes place, followed by dissociation and absorption of free diclofenac.

EXAMPLE 4

Lornoxicam (3,71 g) and alpha-cyclodextrin (24,30 g) are screened (30 mesh) and tumble mixed. The mixture is transferred to a mortar. Deionised water (10–15 ml) is gradually added with vigorous mixing to produce a uniform paste. Vigorous mixing is continued for 1 hour. The mixture is dried in vacuo at 40° C. The dried mass is crushed and passed through 30 mesh screen. The powder is homogenized in a tumble mixer for 10 minutes. The product contains 13% by mass lornoxicam.

EXAMPLE 5

The inclusion complex of alpha-cyclodextrin-lornoxicam obtained in Example 4 was formulated into tablets with the following unit composition:

| | |
|---|---|
| Lornoxicam-alpha-cyclodextrin complex (equivalent to 4 mg lornoxicam) | 30,2 mg |
| Tromethamine | 30,0 mg |
| Microcrystalline cellulose | 26,2 mg |
| Starch | 12,4 mg |
| Magnesium stearate | 1,2 mg |
| TOTAL | 100 mg |

The tablets were prepared as described in Example 2.

FIG. 2 is a graph of the mean dissolution rate of 6 lornoxicam-alpha cyclodextrin tablets prepared according to Example 5. The dissolution rate in purified water (pH ~6.5, temperature 37° C.) with a paddle speed of 50 rpm shows that 80% is dissolved within 30 minutes. The release rate of lornoxicam from the system is consistent with pharmacopoeal specifications for highly soluble drugs (e.g. 80% dissolved within 45 minutes) indicating the solubilizing potential of tablets prepared according to the invention.

The pharmaceutical composition of the invention is preferably for use in the treatment of acute pain and inflammation.

We claim:

1. A pharmaceutical composition for oral administration in solid oral dosage form comprising an inclusion complex of a non-steriodal anti-inflammatory drug selected from the group consisting of diclofenac, indomethacin, naproxen, ibuprofen. mefenamic acid, piroxicam, tenoxicam, lornoxicam, or a pharmaceutically acceptable salt thereof and a cyclodextrin, the mass ratio of the non-steriodal anti-inflammatory drug to cyclodextrin in the inclusion complex being between 1:0.85 and 1:5 inclusive, and a physiologically acceptable alkali agent selected from the group consisting of alkali and alkaline earth metal carbonates, bicarbonates and phosphates, and water soluble amines, in an amount equivalent to between 15 and 30 molar equivalents inclusive of the non-steriodal anti-inflammatory drug, the alkali agent being present in sufficient amount to form an alkaline diffusion layer around the composition in the gastrointestinal tract and the composition being free from any added acid agent which will form an acid-base couple with the alkali agent so as to render the alkali agent incapable of forming said alkaline diffusion layer and wherein said dosage form is either a tablet or a capsule.

2. A pharmaceutical composition according to claim 1 wherein the cyclodextrin is selected from the group consisting of an alpha-cyclodextrin, an unsubstituted beta-cyclodextrin, and a substituted beta-cyclodextrin.

3. A pharmaceutical composition according to claim 1 wherein the alkali agent is sodium bicarbonate.

4. A pharmaceutical composition according to claim 1 wherein the alkali agent is tromethamine.

5. A pharmaceutical composition according to claim 1 wherein the mass ratio of the non-steroidal anti-inflammatory drug to cyclodextrin in the inclusion complex is between 1:1 and 1:2.5 inclusive.

6. A pharmaceutical composition according to claim 1 wherein the inclusion complex is an inclusion complex of diclofenac or a pharmaceutically acceptable salt thereof and an unsubstituted beta-cyclodextrin.

7. A pharmaceutical composition according to claim 6 wherein the mass ratio of diclofenac to beta-cyclodextrin is between 1:1.8 and 1:9 inclusive and the unit dose of the complex is equivalent to between 10 and 100 mg inclusive diclofenac.

8. A pharmaceutical composition according to claim 7 wherein the mass ratio of diclofenac to beta-cyclodextrin is between 1:3 and 1:5 inclusive and the unit dose of the complex is equivalent to between 20 and 60 mg inclusive diclofenac.

9. A pharmaceutical composition according to claim 1 wherein the inclusion complex is an inclusion complex of lornoxicam and alpha-cyclodextrin.

10. A pharmaceutical composition according to claim 9 wherein the mass ratio of lornoxicam to alpha-cyclodextrin is between 1:2.6 and 1:13 inclusive and the unit dose of the complex is equivalent to between 2 and 10 mg inclusive lornoxicam.

11. A pharmaceutical composition according to claim 1 which includes a further active ingredient selected from the group consisting of morphine, codeine, propoxyphene, paracetamol, and meprobamate.

12. A pharmaceutical composition according to claim 1 which includes one or more conventional excipients.

* * * * *